United States Patent [19]

Witzig et al.

[11] 4,431,411

[45] Feb. 14, 1984

[54] SEGMENTED LABIAL BOW WITH LIP PADS FOR AID IN THE CORRECTION OF CLASS III MALOCCLUSIONS AND MALOCCLUSIONS WITH UNDERDEVELOPED MAXILLAS

[76] Inventors: John W. Witzig, 2040 Douglas Dr., N., Golden Valley, Minn. 55422; James A. Evans, 1602 W. Blvd., Rapid City, S. Dak. 57701

[21] Appl. No.: 325,640

[22] Filed: Nov. 30, 1981

[51] Int. Cl.³ ................................................ A61C 7/00
[52] U.S. Cl. .......................................................... 433/6
[58] Field of Search ............................................. 433/6

[56] References Cited
U.S. PATENT DOCUMENTS 3,925,894 12/1975 Robins .................................... 433/6
4,026,023 5/1977 Fisher ..................................... 433/7
4,299,568 11/1981 Crowley ................................. 433/6

Primary Examiner—Robert Peshock
Attorney, Agent, or Firm—Malcolm Reid

[57] ABSTRACT

A segmented labial bow with lip pads for use in the correction of Class III malocclusions and malocclusions with underdeveloped maxillas. The segmented labial bow with lip pads is attached to a conventional orthopedic/orthodontic appliance. As the orthopedic/orthodontic appliance is activated, the lip pads on the segmented bow hold the upper lip away from the roots of the maxillary anterior teeth and alveolar process allowing skeletal development of the premaxillary area with resultant forward movement of the roots and alveolar bone of the premaxillary teeth.

13 Claims, 2 Drawing Figures

SEGMENTED LABIAL BOW WITH LIP PADS FOR AID IN THE CORRECTION OF CLASS III MALOCCLUSIONS AND MALOCCLUSIONS WITH UNDERDEVELOPED MAXILLAS

BACKGROUND OF THE INVENTION AND SUMMARY

The present invention relates to an active orthopedic appliance for aiding in the correction of Class III malocclusions and malocclusions with underdeveloped maxillas and, more particularly, to an improvement to conventional orthopedic correctors employed by orthodontists to correct Class III type malocclusions. A Class III malocclusion is defined as a malposition of the maxillary and mandibular teeth and denture bases so that the lower arch is anterior to the upper arch, resulting in an esthetically unattractive face. An underdeveloped maxilla is a maxilla that is deficient anterioposteriorly, thereby giving the face and teeth a Class III appearance. The characteristics of this type of malocclusion are a long mandibular body, frequently underdeveloped maxilla, and maxillary incisors occluding lingually to the mandibular incisors or a combination thereof.

The basic objectives of treatment for a Class III malocclusion or underdeveloped maxilla are:

1. Eliminate the forced bite;
2. Retard excessive mandibular growth horizontally; and
3. Stimulate all possible anterior-posterior development of the maxilla, if it is underdeveloped.

If there is maxillary underdevelopment, the use of a functional, removable active orthopedic appliance has proven to be efficient in restoring normal arch form and size through the medium of expansion. The general philosophy of treatment is to eliminate all restricting influences on the maxilla and thereby obtain the greatest possible potential of the normal growth and development pattern. The use of fixed appliances, such as braces and chin caps with extra oral force to exert a retruding pressure on the mandible, has proven effective and may be used in conjunction with a functional, removable active orthopedic appliance in the treatment of a Class III malocclusion.

During treatment of certain Class III type malocclusion cases with an orthopedic appliance, the crowns of the premaxillary teeth are moved anteriorly. However, due to the nature of the orthopedic appliance and the pressure of the lips on the gingiva and the alveolar process, the roots of the premaxillary teeth remain unmoved. This results in an inclination of the premaxillary teeth which is not cosmetically pleasing and which often results in a relapse of the premaxillary teeth to their original position.

The present invention uses a segmented bow with acrylic pads affixed to the ends of each of two segments to reduce the lip pressure and thereby allow a translatory movement of the maxillary teeth and alveolar process. The segmented bows may be attached to the sides of the active orthopedic appliance with solder or suspended on a wire originating in the acrylic portion of the appliance. The two segments are extended from their points of attachment around the perimeter of the gum of the premaxillary segment. The bow is segmented or split. In other words, the bow is not continuous from point of attachment on one side of the appliance around the perimeter of the gums to the point of attachment on the other side of the appliance. The purpose of the split bow as opposed to a continuous bow is to allow more flexing movements of the bow, thereby alleviating pain and irritation to the patient. Prior to the use of the segmented labial archwire with acrylic pads of the present invention, it was common to initiate orthognathic surgery to move bone and premaxillary teeth forward. It has been found that patient cooperation with the use of the present invention is excellent, partially due to the fact that it is painless. An orthodontist is especially concerned with the level of patient cooperation because the patient is actively involved in the treatment through the required care and activation of the appliance and the frequency and duration of wearing the appliance. Any pain experienced by a patient expectedly results in less frequent use of the appliance and lesser duration of use.

The appliance of the present invention may also be outfitted with various orthodontic attachments, such as lingual archwires or springs, to induce the movement of individual teeth.

IN THE DRAWINGS

DESCRIPTION OF A PREFERRED EMBODIMENT

Figure 1:
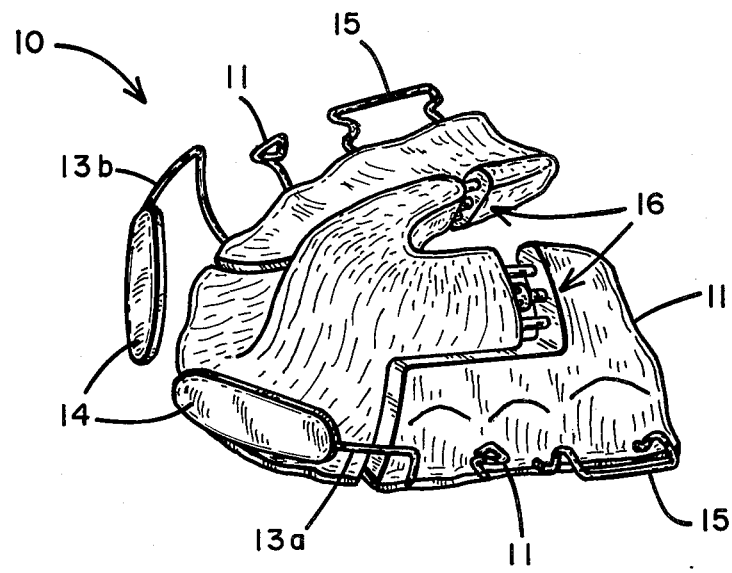
FIG. 1 is a perspective view from the anterior side quarter of an orthopedic appliance with a segmented labial bow and acrylic lip pads.

Referring to the drawings, there is shown in FIG. 1 an orthopedic appliance indicated generally at 10 according to the present invention. The portion of the appliance which fits in the patient's palate is indicated at 11 and referred to as the palatal portion of the appliance. It is made of acrylic. The palatal portion is molded to conform to the patient's mouth, using established techniques of the dental laboratory. With one such technique, a plaster cast is made of the patient's mouth and dentition. The palatal portion of the appliance is fabricated to the shape of the plaster cast. Triangular clasps 12 or Adams clasps 15 fasten the palatal portion of the appliance to the teeth and are embedded in the acrylic at the time of molding. These claps are formed to fit on or between each patient's individual teeth to hold the appliance 10 in place. The palatal portion 11 of the appliance 10 may also include conventional elements, such as lingual wires, expansion screws 16 and open or closed springs. Such conventional elements or combinations of them can be used to cause buccal, protractional, distal, rotational, or lingual movement of individual teeth or groups of teeth while the dominant effect of the orthopedic appliance is at work; that is, attempting to influence the basal maxilla-mandibular relationship to change from a Class III type malocclusion to a Class I occlusion. The basal maxilla-mandibular relationship is primarily influenced by expansion of the palatal portion 11 of the appliance with bilateral jackscrews 16. As treatment progresses, the jackscrews 16 are expanded, thereby moving the premaxilla forward in relation to the mandible. The jackscrews 16 comprise the active element of the appliance 10. FIG. 1 shows one of the segmented bows 13a extending from the side of the palatal portion 11 of the appliance 10 and extending in an arc towards the anterior portion of the appliance. The other segmented bow 13b extends from the opposite side of the appliance 10 in like manner. Each segment 13a and 13b are terminated in an acrylic pad 14. Each segment 13a and 13b is attached to the palatal portion 11 of the appliance by embedding the end of the wire in the acrylic or other suitable means. The segmented bows are manufactured of stainless steel chromium nickel alloys and non-ferrous metal wire. This blend of non-ferrous wire is used because it is highly resistant to oral acidity. Such wire is commercially available in the dental trade.

The segmented bows 13a and 13b are extended upwards from their point of attachment to the palatal portion 11 of the appliance 10 to the extent necessary to arc between the upper lip 16 and the upper gum tissue without coming in contact with the upper gum tissue. The acrylic pads 14 are, therefore, also positioned between the upper lip 16 and the upper gums. The acrylic pads 14 are projected outward so that they come in contact with the upper lip 16 pressuring the upper lip 16 away from the upper gum tissue.

The acrylic on the palatal portion 11 of the appliance 10 may or may not cover the occlusal or biting surface of the upper posterior teeth. The acrylic on the palatal portion 11 does, however, come in contact with the crowns on the upper posterior teeth. If the upper incisors are locked inside the lower incisors, the acrylic covering serves the function of allowing the upper front teeth to move forward without having interference or stoppage from the lower teeth.

DESCRIPTION OF OPERATION OF PREFERRED EMBODIMENT

The orthopedic appliance 10 is, as its name implies, a device for orthopedic correction as opposed to orthodontic correction. The appliance can be outfitted with various conventional elements to accomplish orthodontic correction during the same period of time that orthopedic correction is taking place. Naturally, it is more economical to accomplish both corrections concurrently and preferable from the patient's point of view.

After the orthopedic appliance 10 has been molded to fit the individual patient's mouth by conventionally used techniques, the orthopedic appliance 10 is placed in the roof of the patient's mouth. It must be emphasized that an orthopedic appliance 10 is a device which must be specially made to fit each individual's mouth. The segmented bows 13a and 13b with lip pads 14 are adjusted after insertion in the patient's mouth so that the lip pads exert gentle pressure against the patient's upper lip 16. The upper lip 16 is thereby held away from the gum tissue of the premaxillary segment. After activating the palatal portion 11 of the appliance 10, causing the premaxilla and the premaxillary teeth to be moved anteriorly and the pressure of the upper lip 16 to be removed from the gums, it is believed that the muscles which attach to the periosteum which lies between the gum tissue and the bone of the premaxillary segment are pulled away from the periosteum. The palatal portion 11 is activated by expanding the jackscrews 16 in stages as treatment progresses. The resulting tension at the point where the muscles connect to the periosteum causes appositional growth of the bone on the facial surface of the premaxillary segment. The forward growth of the bone in the premaxillary segment carries the roots of the premaxillary dentition forward.

From time to time as the forward growth progresses, the clinician is required to adjust the lip pads 14. Adjustment is generally in an anterior direction. The segmented bows 13a and 13b are more flexible than a continuous bow and, therefore, causes less discomfort to the patient as conditions in the patient's mouth change from time to time. The lip pads 14 are also intended to facilitate patient comfort by distributing the force across a wide area of the inside upper lip 16.

The embodiments of the invention in which an exclusive property or privilege is claimed are defined as follows:

1. An orthopedic appliance for removing lip pressure from the premaxillary gum tissue for aiding in the correction of Class III type malocclusions comprising:
   a. a palatal appliance;
   b. a segmented bow consisting of two segments, each segment attached to opposite sides of a palatal appliance and extending along without contacting the premaxillary gum tissue of a patient between the premaxillary gum tissue and the upper lip to a point of disjuncture of the two segments at the extreme anterior of the premaxillary gum tissue; and
   c. two pads, each attached at the respective ends of the two segments at the extreme anterior of the premaxillary gum tissue and in contact with the inner surface of the upper lip.

2. The orthopedic appliance of claim 1 wherein each of the segments of the bow is manufactured of stainless steel chromium-nickel alloys and non-ferrous metals.

3. The orthopedic appliance of claim 1 wherein the palatal appliance is removable.

4. The orthopedic appliance of claim 1 wherein the palatal appliance is manufactured of acrylic.

5. The orthopedic appliance of claim 1 wherein the pads are manufactured of acrylic.

6. An orthopedic appliance for removing lip pressure from the premaxillary gum tissue for aiding in the correction of Class III type malocclusions comprising:
   a. a palatal appliance;
   b. a bow attached to opposite sides of a palatal appliance and extending along without contacting a portion of the perimeter of the premaxillary gum tissue of a patient between the premaxillary gum tissue and the upper lip; and
   c. a pad attached at the end of the bow and in contact with the inner surface of the upper lip.

7. The orthopedic appliance of claim 6, wherein the bow is manufactured of stainless steel chromium-nickel alloys and non-ferrous metals.

8. The orthopedic appliance of claim 6, wherein the palatal appliance is removable.

9. The orthopedic appliance of claim 6, wherein the palatal appliance is manufactured of acrylic.

10. The orthopedic appliance of claim 6, wherein the pad is manufactured of acrylic.

11. A method for aiding in the influencing of the basal maxilla-mandibular relationship from a Class III type malocclusion to a Class I occlusion by removing lip pressure from the premaxillary gum tissue which comprises:
    a. forming an orthopedic appliance molded to fit the upper mouth and dentition of the patient to be treated having a segmented bow consisting of two segments, each segment attached to opposite sides of a palatal appliance and extending along without contacting a portion of the perimeter of the premaxillary gum tissue of a patient between the premaxillary gum tissue and the upper lip to a point of disjunction of the two segments at the extreme anterior of the premaxillary gum tissue;

b. inserting the orthopedic appliance in the patient's upper mouth; and c. adjusting each of the two segments of the bow outward from time to time during the period of treatment so that the two segments remain in contact with the inner surface of the upper lip.

12. The method of claim 11, wherein each of the two segments of the segmented bow terminate in acrylic pads at the point of disjuncture, the two pads being in contact with the inner surface of the upper lip.

13. An improved orthopedic appliance of the type used for aiding in the correction of Class III type malocclusions comprising:

a. a segmented bow comprised of two segments, each segment attached to opposite sides of the orthopedic appliance and extending along without contacting the premaxillary gum tissue of a patient between the premaxillary gum tissue and the upper lip to a point of disjuncture of the two segments at the extreme anterior of the premaxillary gum tissue; and b. two pads, each attached at the respective ends of the two segments at the extreme anterior of the premaxillary gum tissue and in contact with the inner surface of the upper lip whereby lip pressure is removed from the premaxillary gum tissue and the roots of the premaxillary teeth are allowed to move forward.

* * * * *

UNITED STATES PATENT AND TRADEMARK OFFICE
CERTIFICATE OF CORRECTION

PATENT NO. : 4,431,411

DATED : February 14, 1984

Page 1 of 4

INVENTOR(S) : John W. Witzig et al.

It is certified that error appears in the above-identified patent and that said Letters Patent is hereby corrected as shown below:

The title page showing the illustrative figure should be deleted to appear as per attached title page.

Figure 2:
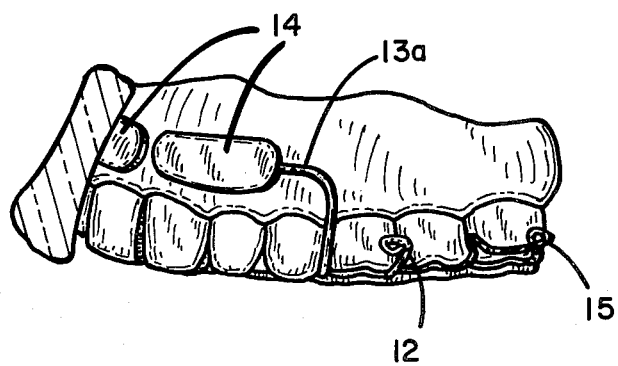
FIG. 2 is a perspective view from the anterior side quarter of an orthopedic appliance with a segmented labial bow and acrylic lip pads shown inserted in a cutaway view of a patient's mouth.
Figure 1:
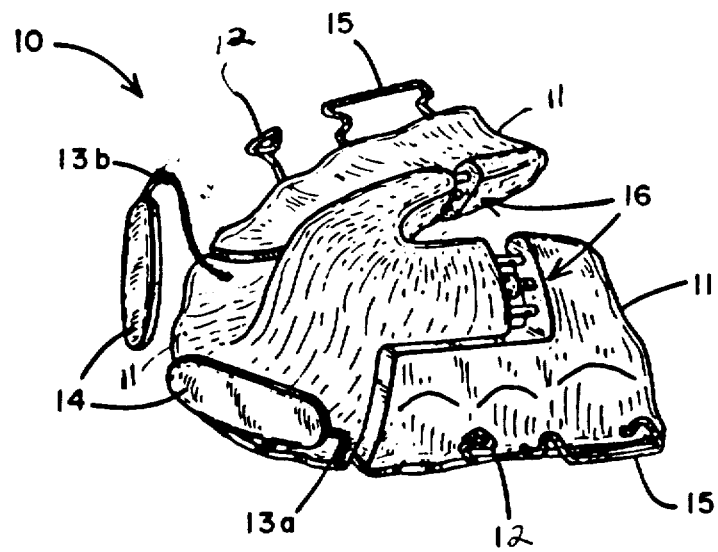
Figure 2:
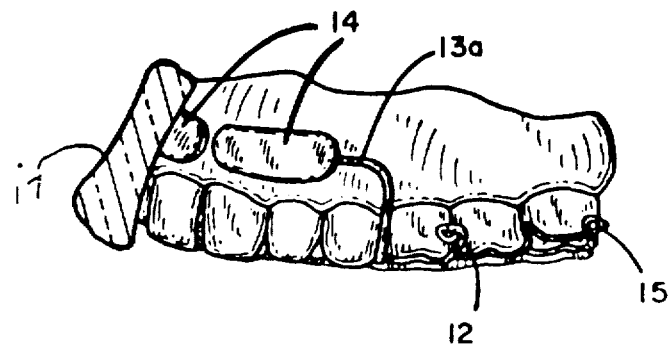

Figures 1 and 2, should appear as shown on the attached sheet.

Signed and Sealed this

Twenty-third Day of April 1985

[SEAL]

Attest:

*Attesting Officer*

DONALD J. QUIGG

*Acting Commissioner of Patents and Trademarks*

UNITED STATES PATENT AND TRADEMARK OFFICE
CERTIFICATE OF CORRECTION

PATENT NO. : 4,431,411

DATED : February 14, 1984

INVENTOR(S) : Witzig and Evans

It is certified that error appears in the above—identified patent and that said Letters Patent is hereby corrected as shown below:

1) Clasp 11 on the sides of the orthodontic appliance 10 are changed from numeral 11 to numeral 12 in Figure 1 as shown in the corrected Figure 1 attached hereto as Figure 1 (corrected);

2) Numeral 11 is added to Figure 1 so that it points to the left side and front part of the palatal part of the orthopedic appliance 10 as well as to the right side as shown in the corrected Figure 1 attached hereto as Figure 1 (corrected);

3) Numeral 17 is added to Figure 2 to designate a segment of the lip as shown in Figure 2 attached hereto as Figure 2 (corrected);

4) In column 3 lines 15, 18 and 20 numeral 16 is changed to numeral 17 in each instance;

5) The following sentence is added at the end of the sentence in line 2, column 3 --The segmented bows can also be connected to the sides of the moveable front of the palatal portion 11 of the appliance 10.--; and 6) Segments 13a and 13b are connected to the appliance 10 as shown in the corrected Figures 1 and 2 attached hereto as Figures 1(corrected) and 2(corrected).

United States Patent [19]

Witzig et al.

[11] 4,431,411
[45] Feb. 14, 1984

[54] SEGMENTED LABIAL BOW WITH LIP PADS FOR AID IN THE CORRECTION OF CLASS III MALOCCLUSIONS AND MALOCCLUSIONS WITH UNDERDEVELOPED MAXILLAS

[76] Inventors: John W. Witzig, 2040 Douglas Dr., N., Golden Valley, Minn. 55422; James A. Evans, 1602 W. Blvd., Rapid City, S. Dak. 57701

[21] Appl. No.: 325,640

[22] Filed: Nov. 30, 1981

[51] Int. Cl.³ .............................................. A61C 7/00
[52] U.S. Cl. ..................................................... 433/6
[58] Field of Search ........................................ 433/6

[56] References Cited

U.S. PATENT DOCUMENTS 3,925,894 12/1975 Robins ................................... 433/6
4,026,023 5/1977 Fisher ..................................... 433/7
4,299,568 11/1981 Crowley ................................. 433/6

Primary Examiner—Robert Peshock
Attorney, Agent, or Firm—Malcolm Reid

[57] ABSTRACT

A segmented labial bow with lip pads for use in the correction of Class III malocclusions and malocclusions with underdeveloped maxillas. The segmented labial bow with lip pads is attached to a conventional orthopedic/orthodontic appliance. As the orthopedic/orthodontic appliance is activated, the lip pads on the segmented bow hold the upper lip away from the roots of the maxillary anterior teeth and alveolar process allowing skeletal development of the premaxillary area with resultant forward movement of the roots and alveolar bone of the premaxillary teeth.

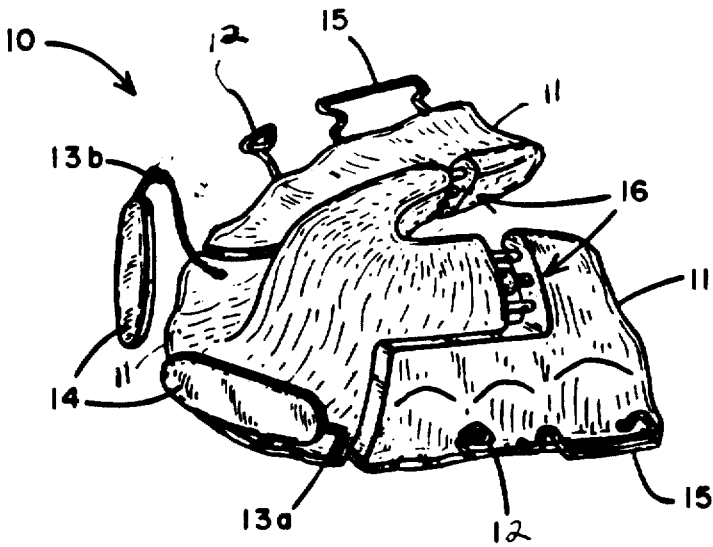

13 Claims, 2 Drawing Figures